US00PP33931P2

(12) United States Plant Patent
Kievit et al.

(10) Patent No.: US PP33,931 P2
(45) Date of Patent: Feb. 1, 2022

(54) ***LYSIMACHIA* PLANT NAMED 'NIGHT LIGHT'**

(50) Latin Name: *Lysimachia alfredii*
Varietal Denomination: Night Light

(71) Applicant: Ball Horticultural Company, West Chicago, IL (US)

(72) Inventors: Christa Kievit, Hem (NL); Karl F. Batschke, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/460,266

(22) Filed: Aug. 29, 2021

(51) Int. Cl.
*A01H 6/00* (2018.01)
*A01H 5/02* (2018.01)

(52) U.S. Cl.
USPC ..... Plt./453

(58) Field of Classification Search
USPC ..... Plt./453
See application file for complete search history.

*Primary Examiner* — Annette H Para
(74) *Attorney, Agent, or Firm* — Audrey Charles

(57) ABSTRACT

A new and distinct cultivar of *Lysimachia* plant named 'Night Light', characterized by its dark yellow-colored flowers, dark green and dark burgundy colored foliage, having light green-colored venation; and moderately vigorous, mounded-spreading growth habit, is disclosed.

1 Drawing Sheet

Latin name of genus and species of plant claimed: *Lysimachia alfredii.*

Variety denomination: 'Night Light'.

BACKGROUND OF THE INVENTION

The present invention relates to a new and distinct cultivar of *Lysimachia* plant botanically known as *Lysimachia alfredii* and hereinafter referred to by the cultivar name 'Night Light'.

The new cultivar originated in a controlled breeding program in Hem, the Netherlands during July 2016. The objective of the breeding program was the development of *Lysimachia* cultivars for use as an accent plant in a container or a flowering groundcover in shade to partial shade landscapes.

The new *Lysimachia* cultivar is the result of self-pollination. The parent of the new cultivar is the proprietary *Lysimachia alfredii* breeding selection coded B009, not patented, characterized by its medium yellow-colored flowers, medium green-colored foliage having slightly darker green-colored venation, and vigorous, spreading-trailing growth habit. The new cultivar was selected as a single flowering plant within the progeny of the above stated self-pollination during August 2017 in a controlled environment in Hem, the Netherlands.

Asexual reproduction of the new cultivar by terminal stem cuttings since August 2017 in Hem, the Netherlands and West Chicago, Ill. has demonstrated that the new cultivar reproduces true-to-type with all of the characteristics, as herein described, firmly fixed and retained through successive generations of such asexual propagation.

SUMMARY OF THE INVENTION

The following characteristics of the new cultivar have been repeatedly observed and can be used to distinguish 'Night Light' as a new and distinct cultivar of *Lysimachia* plant:

1. Dark yellow-colored flowers;
2. Dark green and dark burgundy colored foliage, having light green-colored venation; and
3. Moderately vigorous, mounded-spreading growth habit.

Plants of the new cultivar differ from plants of the parent primarily in having darker green and dark burgundy colored foliage, having green and white venation, reduced growth vigor, and a more mounded growth habit.

Of the many commercially available *Lysimachia* cultivars, the most similar in comparison to the new cultivar is 'Persian Chocolate', not patented. However, in side-by-side comparison, plants of the new cultivar differ from plants of 'Persian Chocolate' in at least the following characteristics:

1. Plants of the new cultivar have light, green-colored venation unlike than plants of 'Persian Chocolate';
2. Plants of the new cultivar have a leaf color that has less burgundy coloration under shade conditions than plants of 'Persian Chocolate'; and
3. Plants of the new cultivar are taller than plants of 'Persian Chocolate'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Night Light'. The plants were approximately 20 weeks old. The plants were grown three plants per pot in three-quart containers for approximately 12 weeks in an outdoor shade nursery in West Chicago, Ill. Plants were given two pinches prior to transplant and one pinch one week after transplant.

DETAILED BOTANICAL DESCRIPTION

Figure 1:
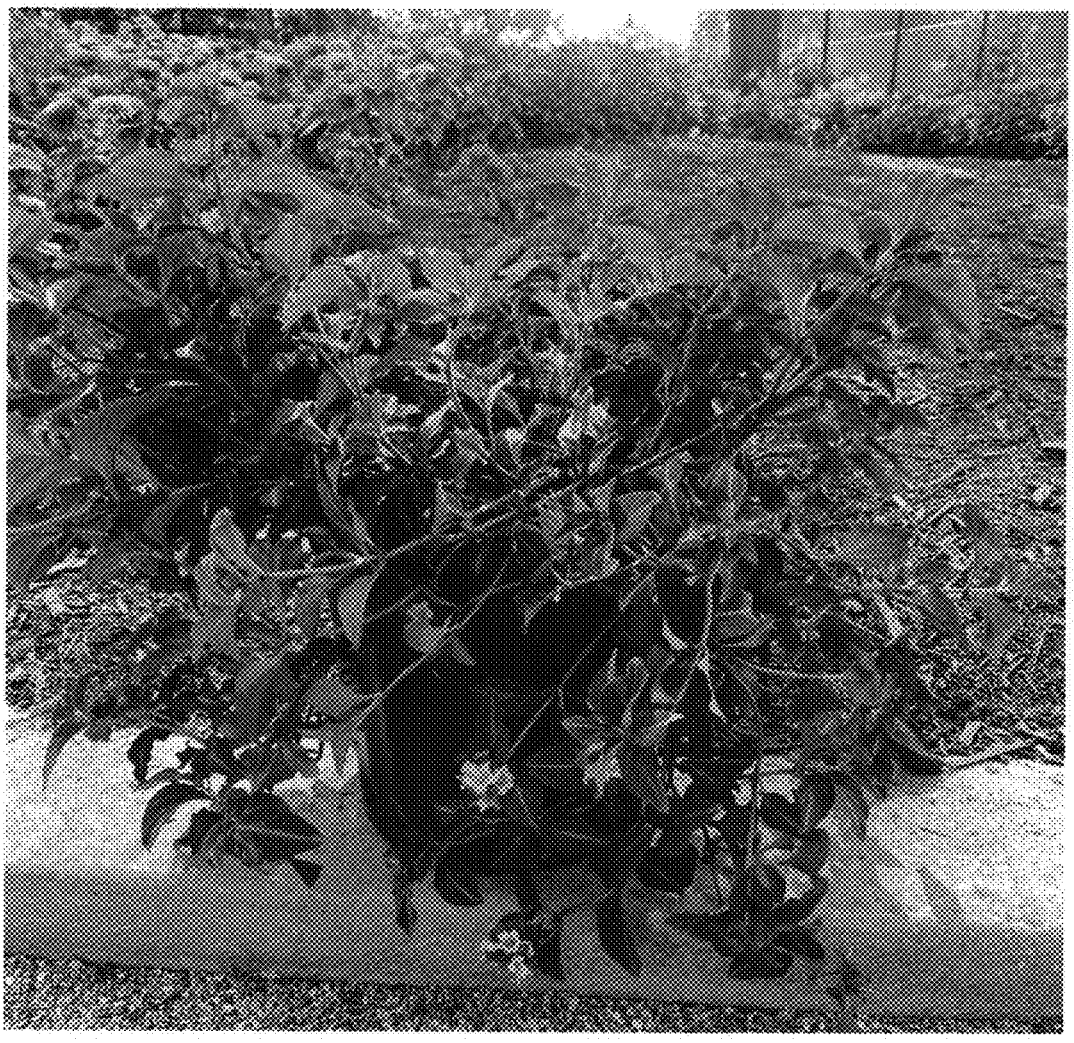
FIG. 1 illustrates a side view of the overall growth and flowering habit of 'Night Light'.
Figure 2:
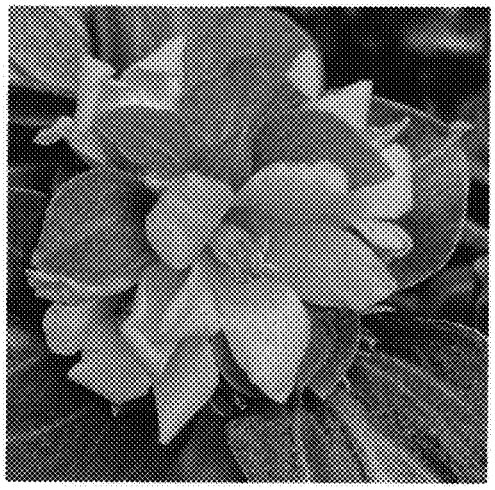
FIG. 2 illustrates a close-up view of an individual inflorescence of 'Night Light'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2021 under natural light conditions in Naperville, Ill.

The following descriptions and measurements describe approximately 20-week old plants produced from cuttings from stock plants and grown under conditions comparable to those used in commercial practice. The plants were grown three plants per pot in three-quart containers for approximately 12 weeks in an outdoor shade nursery in West Chicago, Ill. Plants were given two pinches prior to transplant and one pinch one week after transplant. Prior to transplant plants were grown in liners in a poly-covered greenhouse in West Chicago, Ill. Greenhouse temperatures ranged from an average high of 79.5° F. (26.4° C.) to an average low of 68.5° F. (20.3° C.), and supplemental lighting was provided daily for five hours during short days. Measurements and numerical values represent averages of typical plants.

Botanical classification: *Lysimachia alfredii* 'Night Light'.

Parentage:

*Female and male parent*.—Proprietary *Lysimachia alfredii* breeding selection coded B009, not patented Propagation:

*Type cutting*.—Terminal stem.

*Time to initiate roots*.—Approximately 7 days.

*Time to produce a rooted cutting*.—Approximately 42 to 49 days.

*Root description*.—Fibrous.

*Rooting habit*.—Freely branching.

Plant description:

*Commercial crop time*.—Approximately 6 to 8 weeks from a rooted cutting to finish in a 10 cm pot.

*Growth habit and general appearance*.—Perennial, flowering groundcover, moderately vigorous, mounded-spreading.

*Hardiness*.—USDA Zone 5b (−15° F. to −10° F./−26.1° C. to −23.3° C.).

*Size*.—Height: Approximately 24.0 cm. Width: Approximately 49.0 cm.

*Branching habit*.—Freely basal branching, pinching enhances basal branching. Quantity of main branches per plant: Approximately 16.

*Branch*.—Strength: Strong, flexible. Length: Approximately 33.0 cm. Diameter: Approximately 3.0 mm. Length of central internode: Approximately 6.0 cm. Texture: Densely pubescent. Color of young and mature stems: 146B with a heavy overlay of 187A.

Foliage description:

*General description*.—Quantity of leaves per branch: Approximately 16. Fragrance: Slight. Form: Simple. Arrangement: Opposite.

*Leaves*.—Aspect: Perpendicular to oblique angle to stem. Shape: Ovate. Margin: Entire, slightly wavy. Apex: Acute. Base: Rounded. Venation pattern: Pinnate. Length of mature leaf: Approximately 6.0 cm. Width of mature leaf: Approximately 3.6 cm. Texture of upper surface: Moderately pubescent. Texture of lower surface: Densely pubescent. Color of upper surface of young and mature foliage: NN137A with 137A to 137B, typically tinted with 187A, venation of 138B to 138D. Color of lower surface of young and mature foliage: Closest to 147B mottled with 187A, venation indistinguishable except for midvein of 147C.

*Petiole*.—Length: Approximately 1.0 cm. Diameter: Approximately 2.0 mm. Texture: Moderately pubescent. Color: Closest to 147C mottled with 187A.

Flowering description:

*Flowering habit*.—'Night Light' is freely flowering under outdoor growing conditions with substantially continuous blooming from spring through fall.

*Lastingness of individual flower on the plant*.—Approximately 12 to 14 days.

Inflorescence description:

*General description*.—Type: Terminal raceme, shortened into capitate clusters, each flower subtended by a bract. Quantity of open inflorescences per plant: Approximately 3. Quantity of developing inflorescences per plant: Approximately: 2. Fragrance: None detected. Length or height: Approximately 2.0 cm. Width: Approximately 3.0 cm. Quantity of fully open flowers per inflorescence: Approximately 4 to 6.

*Peduncle*.—Strength: Strong. Aspect: Erect. Length: Approximately 2.2 cm. Diameter: Approximately 2.0 mm. Texture: Densely pubescent. Color: 146B with a heavy overlay of 187A.

Flower description:

*General description*.—Type: Single, upward to outward facing.

*Bud*.—Rate of opening: Generally takes 3 to 4 days for bud to progress from first color to fully open flower. Quantity developing buds per inflorescence: Approximately 4.

*Bud just before opening*.—Shape: Ovoid. Length: Approximately 9.0 mm. Width: Approximately 5.0 mm. Texture: Densely pubescent. Color: Petal portion 7C.

*Corolla*.—Shape: Cup-shaped. Diameter: Approximately 1.7 cm. Depth: Approximately 1.4 cm.

*Petals*.—Quantity: 5. Shape: Obovate. Appearance: Matte. Margin: Minutely scalloped. Apex: Acute, typically curled downward. Base: Attenuate. Length: Approximately 1.4 cm. Width: Approximately 6.0 mm. Texture of upper and lower surfaces: Glabrous. Color of upper surface when first and fully open: 7A with 34B at base. Color of lower surface when first and fully open: 7C with 34C at base.

*Calyx*.—Shape: Cupped. Diameter at widest point: Approximately 8.0 mm.

*Sepals*.—Quantity per flower: 5, fused at base. Shape: Ovate. Margin: Entire. Apex: Acute. Length: Approximately 8.0 mm. Width: Approximately 3.0 mm. Texture of upper (inner) surface: Glabrous. Texture of lower (outer) surface: Moderately pubescent. Color of upper (inner) surface: 145C to 145D.

Color of upper and lower (outer) surfaces: 145D with 146D mottled with N186A.

*Bracts*.—Shape: Elliptic. Margin: Entire, ciliate, slightly wavy. Apex: Acute. Base: Attenuate. Length: Approximately 2.5 cm. Width: Approximately 1.7 cm. Texture of upper and lower surfaces: Glabrous. Color of upper surface when first and fully open: 137A with venation of 138B to 138D. Color of lower surface when first and fully open: Closest to 147B mottled with N186A and 145D at base, venation indistinguishable.

*Pedicle*.—Strength: Strong, flexible. Aspect: Acute angle to stem. Length: Approximately 1.0 cm. Diameter: Approximately 1.0 mm. Texture: Densely pubescent. Color: 145D mottled with 187A.

*Reproductive organs*.—Androecium: Stamen quantity: 5 per flower. Stamen length: Approximately 8.0 mm, basal portion of 3.0 mm connate enclosing the ovary. Anther shape: Sagittate. Anther length: Approximately 2.0 mm. Anther color: 8B. Filament color: 1C for free portion and 7A for basal connate portion with 34B at base. Pollen amount: Moderate. Pollen color: 7A. Gynoecium: Pistil quantity: 1 per flower. Pistil length: Approximately 8.0 mm. Stigma shape: Rounded. Stigma length: Less than 1.0 mm. Stigma color: 146A. Style length: Approximately 6.0 mm. Style color: Closest to 145D. Ovary length: Approximately 1.5 mm. Ovary texture: Densely pubescent at style attachment. Ovary color: Closest to 145C.

Seed and fruit production: Neither seed nor fruit production has been observed.

Disease and pest resistance: Resistance to pathogens and pests common to *Lysimachia* has not been observed.

What is claimed is:

1. A new and distinct cultivar of *Lysimachia* plant named 'Night Light', substantially as herein illustrated and described.

* * * * *